BEST AVAILABLE COPY

United States Statutory Invention Registration [19]

[11] Reg. Number: H356

Stokes et al. [43] Published: Nov. 3, 1987

[54] EPICARDIAL LEAD HAVING LOW THRESHOLD, LOW POLARIZATION MYOCARDIAL ELECTRODE

[75] Inventors: Kenneth B. Stokes, Minneapolis; Gene A. Borazin, Coon Rapids; Wendy A. Berthelsen, St. Paul, all of Minn.

[73] Assignee: Medtronic, Inc., Minneapolis, Minn.

[21] Appl. No.: 706,213

[22] Filed: Feb. 27, 1985

[51] Int. Cl.[4] ..... A61N 1/00

[52] U.S. Cl. ..... 128/785; 128/419 P

[58] Field of Search ..... 128/419 P, 642, 784–785, 128/803; 604/891, 892

[56] References Cited

U.S. PATENT DOCUMENTS 2,782,786 2/1957 Krasno ..... 128/803

3,750,650 8/1973 Ruttgers ..... 128/642

FOREIGN PATENT DOCUMENTS 0047013 3/1982 European Pat. Off. ..... 128/786

*Primary Examiner*—Deborah L. Kyle

*Assistant Examiner*—Michael J. Carone

*Attorney, Agent, or Firm*—Reed A. Duthler; John L. Rooney; Joseph F. Breimayer

[57] ABSTRACT

An epicardial pacing lead for the delivery of stimulation energy to and the sensing of electrical signals from the myocardium of a human heart. The lead includes an electrode which penetrates the myocardium and serves to anchor the lead to the heart. The lead contains a drug for delivery through the electrode, to the myocardium. The electrode is provided with a bore for passage of the drug to the stimulation and fixation site.

14 Claims, 8 Drawing Figures

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

EPICARDIAL LEAD HAVING LOW THRESHOLD, LOW POLARIZATION MYOCARDIAL ELECTRODE

REFERENCE TO COMMONLY ASSIGNED U.S. PATENTS AND APPLICATIONS

Reference is made to U.S. Pat. No. 4,506,680 issued to Stokes for a Drug Dispensing Body Implantable Lead. Reference is also made to patent application Ser. No. 706,214 by Cannon et al for a Drug Dispensing Body Implantable Lead Employing Absorbent Plug and to patent application Ser. No. 706,215 by Stokes for a Drug Dispensing Body Implantable Lead Employing Molecular Sieves.

BACKGROUND OF THE INVENTION

This invention pertains to electrical stimulation leads in general, and to myocardial pacing leads in particular.

Electrical stimulation of the body for medical purposes is well known in the prior art. An example of a device for this purpose is the well known cardiac pacemaker. In the pacemaker context, as well as other body stimulation contexts, the stimulation energy is delivered to the desired body site by an electrode carrying lead.

Interactions between the lead and body can vitiate the desired effects of the stimulation. For example, biologic reactions encourage fibrosis. In the pacemaking context, fibrosis is believed to be a major factor in the increase in chronic stimulation threshold that is usually experienced. Also, trauma results in inflammation of the tissue to be stimulated. Such inflammation may alter the response of the tissue to the stimulation energy, both acutely and chronically.

Other interactions between the lead and body, while not directly affecting the response of the tissue to the stimulation energy, can result in the occurrence of undersirable events. In some circumstances where electrical body stimulation is indicated, the body portion to be stimulated is irritable. The placement of a lead may compound this irritability. For example, placement of a pacemaking lead may include a cardiac arrhythmia. The presence of the lead may also promote thrombus formation.

The interactions noted above have long been recognized and efforts made to ameliorate their consequences. For example, the lead may be configured to reduce mechanical trauma and the response of the irritable tissue during lead placement. Materials may be selected for the lead body and electrodes to minimize fibrosis. However, lead configuration must take into account other factors such as the efficiency of the delivery of the stimulation energy, the ease of placement, maintenance of the desired electrode position, and the reliability of the lead over extended periods of time. An accomodation of these interests has resulted in leads whose configuration necessarily results in undesirable interactions between the lead and body.

Undesirable interactions between lead and body are a particular problem in the context of a myocardial lead employing a penetrating electrode of the sort employed by the present invention. Unlike the electrodes of most endocardial leads, penetrating myocardial electrodes are intended to function by insertion into the tissue, rather than by placement against the tissue. As such, the basic mode of operation of these electrodes requires some small amount of tissue damage to accompany attachment of the electrode. The greater the reaction of the heart tissue to this injury, the more likely it is that subsequent problems of increased threshold, fibrosis or irritability will rise.

It is also known that a systemic treatment with steroids results in acute reduction in the stimulation threshold. In particular, systemic use of glucocorticosteroids has been used to treat chronic exit block, a condition in which the heart tissue's reaction to the pacing lead can result in a chronic rise of the stimulation threshold above the output level of the implanted pacemaker. However, long term systemic use of such steroids produces undesirable side effects.

In particular, copending commonly assigned Application Ser. No. 476,436 referenced above discloses an endocardial pacing lead adapted to dispense a glucocorticosteroid adjacent the stimulation site.

SUMMARY OF THE INVENTION

The present invention provides a body implantable lead for the delivery of stimulation energy to a desired body site. A drug dispenser carried by the lead includes a chamber for retaining the drug to be dispensed, while allowing dispensing of that drug at the desired body stimulation site, in an effort to reduce or eliminate the effects of tissue reaction to the electrode at the stimulation site. The drug may be one intended to counter fibrosis, inflammation, or other undesirable effects of lead placement. In a preferred embodiment, the drug may be the sodium salt of dexamethasone phosphate, a glucocorticosteroid which acts as an anti-inflammatory drug and, which when dispensed by a pacing lead results in the chronic reduction of pacing thresholds.

The preferred embodiment of the lead is an epicardial lead of the sort employing a barbed fixation hook, extending from a flexible base pad. One example of such a lead is the Model 4951 lead, manufactured and sold by Medtronic, Inc. General construction of such a lead is described in commonly assigned U.S. Pat. No. 4,313,448 issued to Stokes and incorporated herein by reference in its entirety. In one preferred embodiment, the fixation hook is hollow, and is provided with entry bores at its proximal end for entry of drug into the electrode, and exit bores at its distal end for delivery of the drug to the tissue to be stimulated. The proximal end of the electrode is mounted within a reservoir which contains the drug. Elution rate may be controlled by the solubility of the drug or by means of a porous, sintered elution path within the electrode itself. In a second embodiment, the hollow hook itself functions as both the drug storage reservoir and the elution path.

This invention and its advantages may be more fully understood in conjunction with the following detailed description.

DESCRIPTION OF THE INVENTION

DETAILED DESCRIPTION OF THE DRAWINGS

Figure 1:
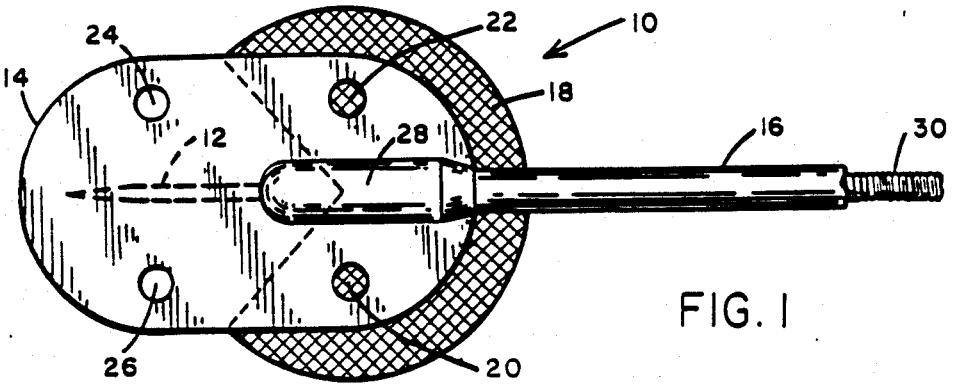
FIG. 1 illustrates a top plan view of a myocardial pacing lead employing the present invention.

FIG. 1 illustrates a top plan view of a generalized form of an epicardial unipolar lead according to the present invention. The lead 10 includes a forward facing, in-line barbed electrode 12 on the underside of a flexible base pad 14 which may be fabricated of polyurethane elastomer or other suitable inert material. The base pad 14 has an elongated rectangular shape with rounded corners and includes a plurality of holes 20, 22, 24 and 26 which may be used for optional placement of sutures. A coiled pacing conductor 30 connects to the shank of the barbed electrode 12 and extends through a substantially centered hole in base pad 14. The coiled conductor 30 consists of a three or four filar coil manufactured of MP35N alloy wire which provides for redundant current paths and a tolerance to flexual stresses. Coil conductor 30 is encapsulated of an insulative sheath 16 of polyether urethane elastomer, silicone rubber or other suitable material which provides an insulator with stretch and flexibility. A surgical mesh 18, having a circumferential portion spanning an arc of approximately 270 degrees from the point electrode 12 passes through base pad 14 provides for fibrous ingrowth. Surgical mesh 18 can be affixed to base pad 14, with suitable adhesive or by other methods.

Figure 2:
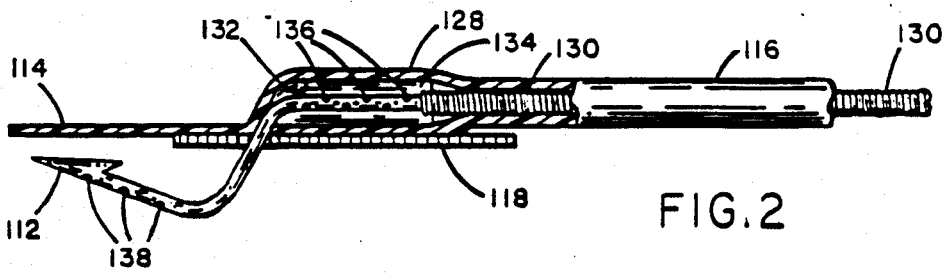
FIG. 2 illustrates a side cut away view of a first embodiment of the distal portion of a pacing lead employing the present invention.

FIG. 2 illustrates a side sectional view of an epicardial lead according to the invention. This illustration shows that lead body 128 is hollow, defining a drug chamber 132, in which a liquid 134 drug is stored. Body fluids enter the drug chamber 132 via electrode 112, diluting drug 134 and allowing it to elute through bores 138 in electrode 112. The liquid drug 134 may be loaded into chamber 132 by means of a hypodermic syringe, inserted through lead body 128. It this is the case, silicone rubber is the preferred material for body 128, as it is substantially self-sealing. For a better seal, the hole caused by the syringe needle may easily be sealed with medical adhesive. This feature would allow the physician to load the drug immediately prior to use, avoiding problems of limited shelf life that might occur if the liquid drug were loaded during manufacture of the electrode. Electrode 112 is also hollow and is provided with a plurality of holes 136 within the drug chamber 132 which serve as entry point for the drug. Holes 138 at the distal portion of the electrode 112 serve as exit points for the drug. The proximal portion of drug chamber 132 may be sealed with medical adhesive or by other appropriate method to prevent leakage proximally along conductor 130.

Figure 3:
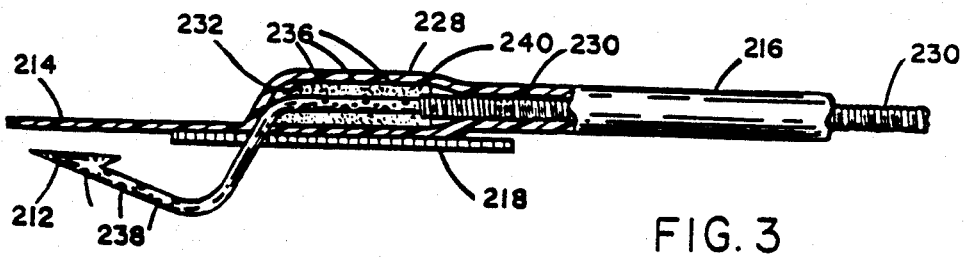
FIG. 3 illustrates a side cut away view of a second embodiment of the distal portion of a pacing lead employing the present invention.

FIG. 3 illustrates a side cut away view of a second embodiment of an epicardial lead according to the invention. This illustration shows that lead body 228 is hollow, defining a drug chamber 232 in which a monolithic controlled release device 240 containing the drug is located. The controlled release device 240 may be fabricated by compounding the drug with a suitable material. For example, sodium dexamethasone phosphate in powder form may be compounded with medical adhesive to form an appropriate monolithic controlled release device. In use, body fluids enter electrode 212 via holes 238 and contact release device 240 via holes 236. The drug diffuses out of release device 240, through needle 212 and is delivered to the stimulation site within the myocardium via holes 238. In this embodiment, the drug is, of course, loaded during manufacturing. All other elements in FIG. 3 correspond to elements in FIG. 2 having the same final two digits.

Figure 4:
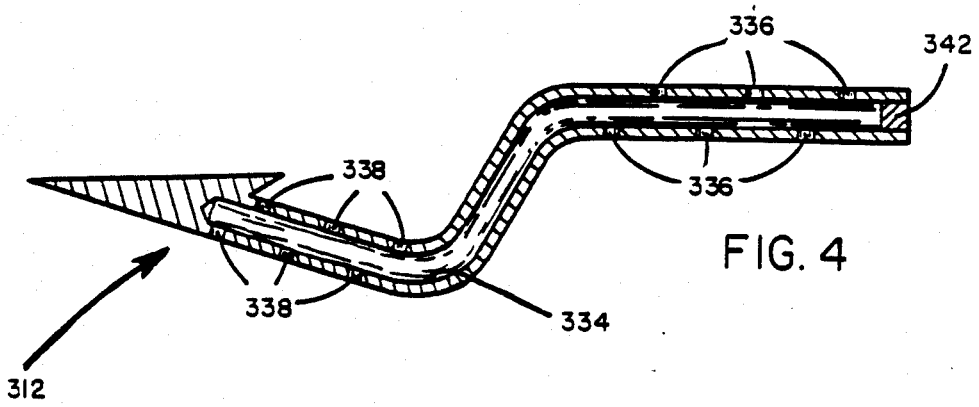
FIG. 4 illustrates a side sectional view of a first embodiment of an electrode for use in the lead of FIG. 2 or FIG. 3.

FIG. 4 shows a side cut away view of an electrode 312, suitable for use with the leads of FIGS. 1 and 2. In this view, the tubular construction of the electrode is disclosed. At the proximal end of electrode 312, plug 342 prevents backflow of drug out of the electrode, and proximally within the lead along conductor 30. Lumen 344 defines an elution path from holes 336 to holes 338.

Figure 5:
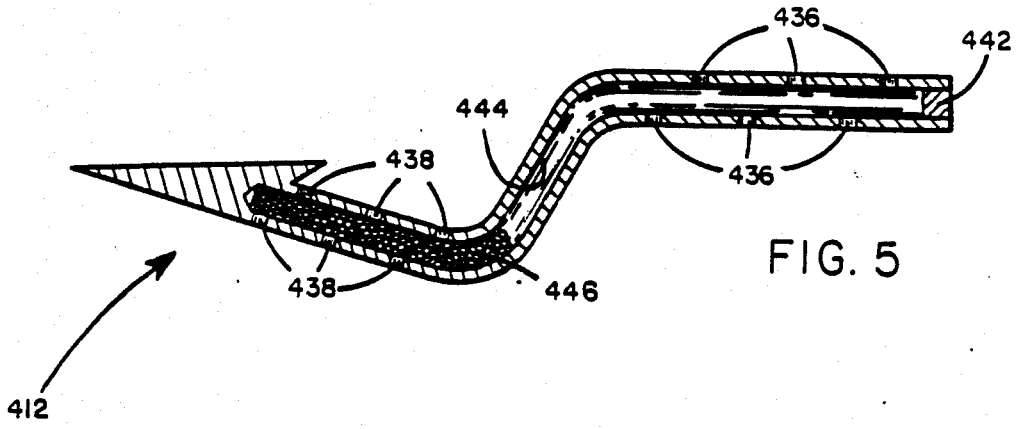
FIG. 5 illustrates a side sectional view of a second embodiment of an electrode for use in the leads of FIG. 2 or FIG. 3.

FIG. 5 shows a side sectional view of a second embodiment of an electrode suitable for use with the leads of FIG. 2 or FIG. 3. In this view, it can be seen that electrode 412 is tubular, and similar in construction to the electrode of FIG. 4. Electrode 412 is provided with a lumen 444 which defines a fluid path from holes 436 at the proximal end of the electrode to holes 438 at the distal end of the electrode. Within the distal end of electrode 412 is located a porous elution path 446, which may be fabricated by filling the central lumen 444 of electrode 412 with metal particles, and sintering them together under high heat to provide a porous structure of known pore size. The pore size chosed for elution path 446 can determine the rate at which the drug exits the electrode.

Figure 6:
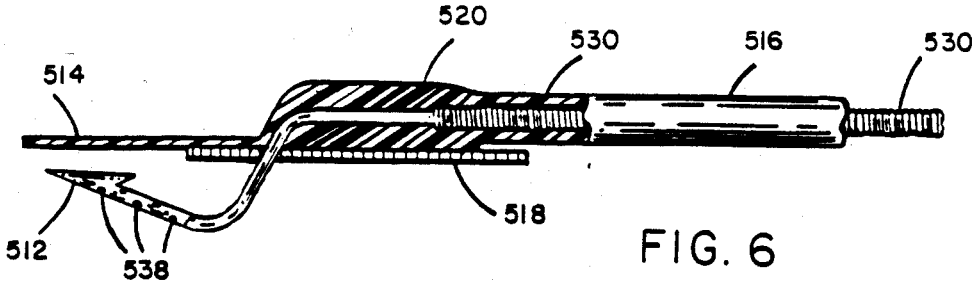
FIG. 6 illustrates a side cut away view of a third embodiment of the distal portion of a pacing lead employing the present invention.

FIG. 6 illustrates a cutaway view of a third embodiment of an epicardial lead according to the present invention. In this view, it can be seen that lead body 528 is solid, rather than hollow. In the embodiment of FIG. 6, the drug is loaded into the central lumen of electrode 512 for elution out of holes 538. All other elements of FIG. 6 correspond to the elements in FIGS. 2 and 3 having the same final two digits.

Figure 7:
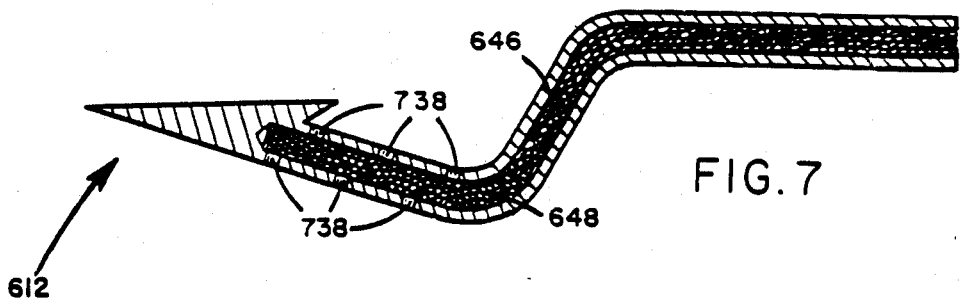
FIG. 7 illustrates a side sectional view of a first embodiment of an electrode for use in the lead of FIG. 6.

FIG. 7 shows a side sectional view of a first embodiment of an electrode for use with the lead of FIG. 6. This electrode is similar in construction to the electrodes of FIGS. 3 and 4, in that it is provided with holes 638 at the distal end of the electrode, and a lumen 646 which defines a fluid pathway. Lumen 646 is completely filled with a porous structure 648, which functions as a drug reservoir, and as a porous elution path. Porous structure 648 may be fabricated by filling lumen 646 of electrode 612 with metal particles and sintering under high heat. In use, the physician dips the distal end of electrode 612 into a solution of the desired drug, which is absorbed into porous structure 648 by capillary action. Later, in use, the drug will diffuse out of electrode 612 at holes 638. This embodiment is advantageous in that it allows the physician to select and load the drug, rather than requiring that the drug be loaded at the factory. As with the embodiment of FIG. 2, this approach avoids problems of limited shelf life due to incorporation of drugs during manufacture.

Figure 8:
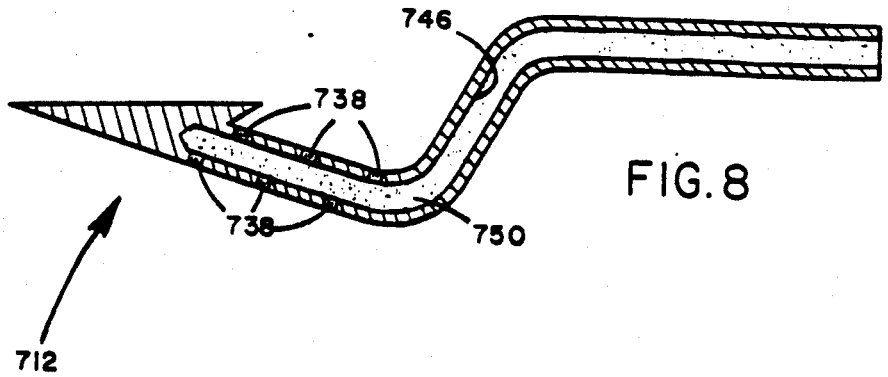
FIG. 8 illustrates a side sectional view of a second embodiment of an electrode for use in the lead of FIG. 6.

FIG. 8 shows a side sectional view of a second embodiment of an electrode for use with the lead of FIG. 6. In this view, electrode 712 is provided with a lumen 746 which defines a drug storage chamber as well as a drug delivery passage way. Within lumen 746 is located a drug 740, which may be fabricated similar to the controlled release device 240 of FIG. 3 or may simply be a powdered form of the drug. In use, drug elutes out electrode 712 to the tissue via holes 738. This embodiment, like the embodiment of FIG. 3, requires that the drug be loaded during manufacture of the lead.

Although the above preferred embodiment is disclosed as a unipolar electrode, bipolar, and other electrode configurations are believed to be within the scope of the invention and within the scope of the following claims.

We claim:

1. In a cardiac pacing lead of the type including an elongated conductor having a proximal end and a distal end, a connector electrically coupled to the proximal end of said conductor, an electrode including fixation means for penetrating the heart tissue, coupled to the distal end of said conductor, and an elongated insulative sheath covering said conductor extending from said electrical connector to said electrode, the improvement wherein:

said electrode includes means for dispensing an anti-inflammatory drug comprising drug storage means for retaining said anti-inflammatory drug and a passageway through which said drug may travel, open to the exterior of said electrode at said fixation means.

2. A pacing lead according to claim 1 wherein the passageway of said dispensing means is provided with porous means for metering the flow of said drug.

3. An electrode according to claim 2 wherein said porous means is fabricated of sintered metal particles.

4. An electrode according to claim 1 wherein said drug storage means comprises porous, absorptive means located within said passage way.

5. A lead according to claim 4 wherein said porous means is fabricated of sintered metal particles.

6. A lead according to claim 1 wherein said drug storage means comprises a drug storage chamber, pierceable by means of a hypodermic syringe whereby said drug storage chamber may be loaded with said drug.

7. A lead according to claim 1 wherein said drug storage means comprises a drug storage chamber, containing said drug compounded in the form of a controlled release means for gradually releasing said drug.

8. In a cardiac pacing lead of the type comprising an elongated conductor having a proximal end and a distal end, a connector electrically coupled to the proximal end of said conductor, an electrode including fixation means for penetrating the heart tissue coupled to the distal end of said conductor, and an elongated insulative sheath covering said conductor, extending from said electrical connector to said electrode, the improvement comprising:

means for dispensing an anti-inflammatory drug at said fixation means comprising a drug storage chamber for retaining said anti-inflammatory drug, and wherein said electrode has a proximal end, located within said drug storage chamber and a distal end bearing said fixation means for penetrating heart tissue, said dispensing means including a passageway through said electrode through which said drug may travel, the passageway of said electrode open to said storage chamber at the proximal end of said electrode and open to the exterior of said electrode at said fixation means at the distal end of said electrode.

9. A pacing lead according to claim 8 wherein said passageway of said electrode is provided with porous means for metering the flow of said drug.

10. An electrode according to claim 9 wherein said porous means is fabricated of sintered metal particles.

11. In a cardiac pacing lead of the type comprising an elongated conductor having a proximal end and a distal end, a connector electrically coupled to the proximal end of said conductor, an electrode including fixation means for penetrating the heart tissue coupled to the distal end of said conductor, and an elongated insulative sheath covering said conductor, extending from said electrical connector to said electrode, the improvement comprising:

means for dispensing an anti-inflammatory drug adjacent said fixation means, comprising a passageway within said electrode, through which said drug may travel, open to the exterior of said electrode at said fixation means, the passageway of said electrode including means for storing said anti-inflammatory drug.

12. A pacing lead according to claim 11 wherein said storage means comprises means for absorbing said drug through said passageway.

13. A lead according to claim 12 wherein said storage means comprises a porous structure fabricated of sintered metal particles.

14. A method of fabricating a cardiac pacing lead of the type including an electrode having a proximal end coupled to an elongated conductor and a distal end including fixation means for penetrating the heart tissue, comprising the steps of:

filling a cardiac electrode of the type including a fixation means and a lumen open to said fixation means with an absorptive material;

coupling said electrode to an electrical conductor; and placing said fixation means of said electrode in a solution of a desired drug, allowing said absorptive substance within said lumen of said electrode to absorb said drug.

* * * * *